(12) United States Patent
Chisena et al.

(10) Patent No.: US 8,277,402 B2
(45) Date of Patent: Oct. 2, 2012

(54) ORTHOPAEDIC DEVICE AND METHOD OF USE FOR TREATING BONE FRACTURES

(76) Inventors: Ernest C. Chisena, Fort Salonga, NY (US); Jahangir S. Rastegar, Stony Brook, NY (US)

( * ) Notice: Subject to any disclaimer, the term of this patent is extended or adjusted under 35 U.S.C. 154(b) by 331 days.

(21) Appl. No.: 12/624,706

(22) Filed: Nov. 24, 2009

(65) Prior Publication Data

US 2011/0125071 A1    May 26, 2011

(51) Int. Cl.
*A61F 5/00*         (2006.01)
(52) U.S. Cl. ........................................... 602/20
(58) Field of Classification Search .................. 602/5, 6, 602/12, 13, 20–21, 23, 26, 62–63; 128/878–879, 128/881
See application file for complete search history.

(56) References Cited

U.S. PATENT DOCUMENTS

| | | | | |
|---|---|---|---|---|
| 3,705,575 A | * | 12/1972 | Edwards | 600/29 |
| 5,171,310 A | * | 12/1992 | Chisena | 602/5 |
| 5,642,739 A | * | 7/1997 | Fareed | 128/881 |

* cited by examiner

*Primary Examiner* — Michael Brown
(74) *Attorney, Agent, or Firm* — Scully, Scott, Murphy & Presser, P.C.

(57) ABSTRACT

Orthopaedic device and a method of use thereof are provided for treating a bone fracture. The orthopaedic device has at least one pressure applying element configured to apply pressure to soft tissue adjacent to the bone fracture and a holder configured to engage, in an engaged configuration, soft tissue adjacent to the bone fracture and, while in the engaged configuration, to permit adjustable positioning and securing the at least one pressure applying element to the holder.

18 Claims, 12 Drawing Sheets

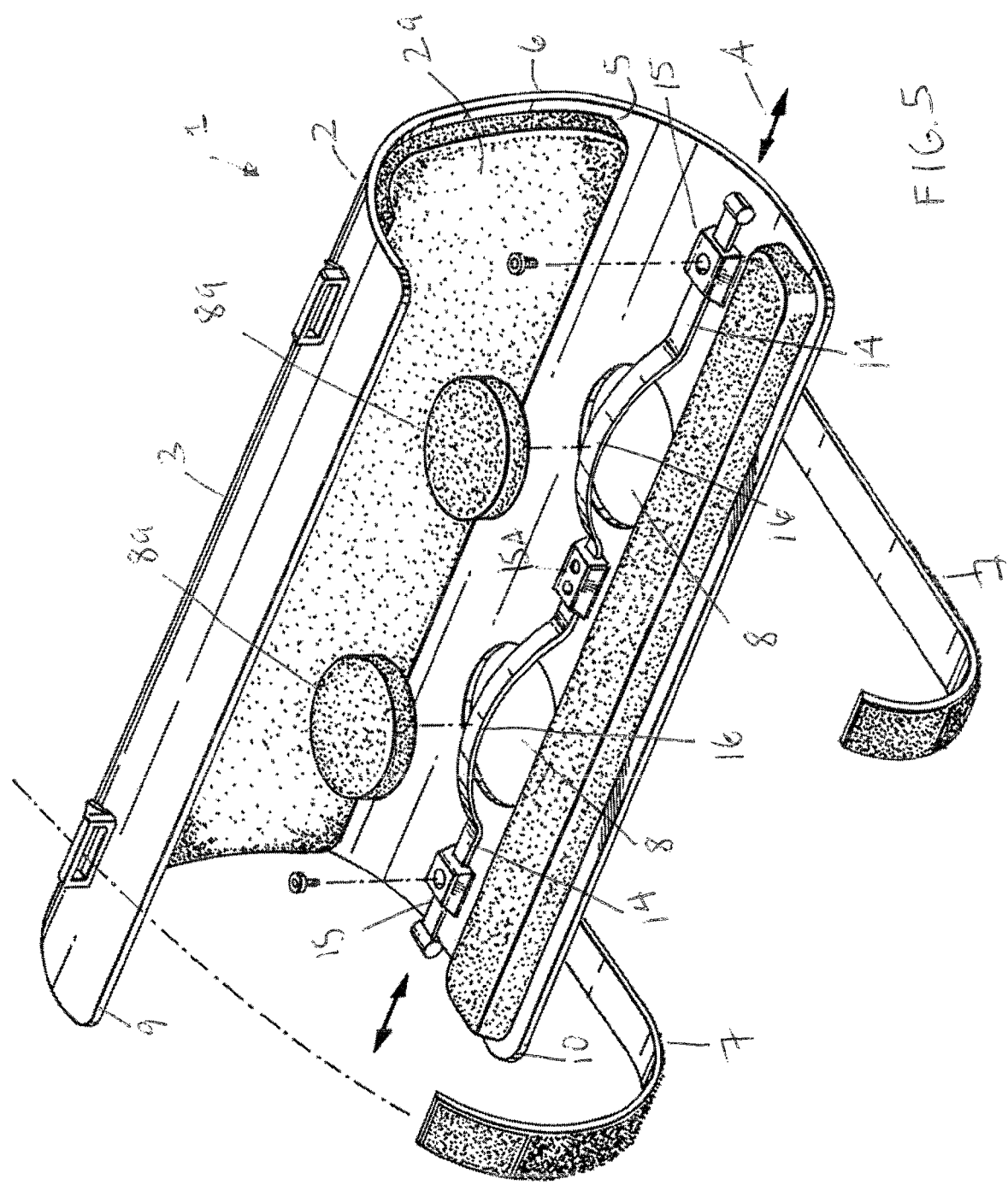

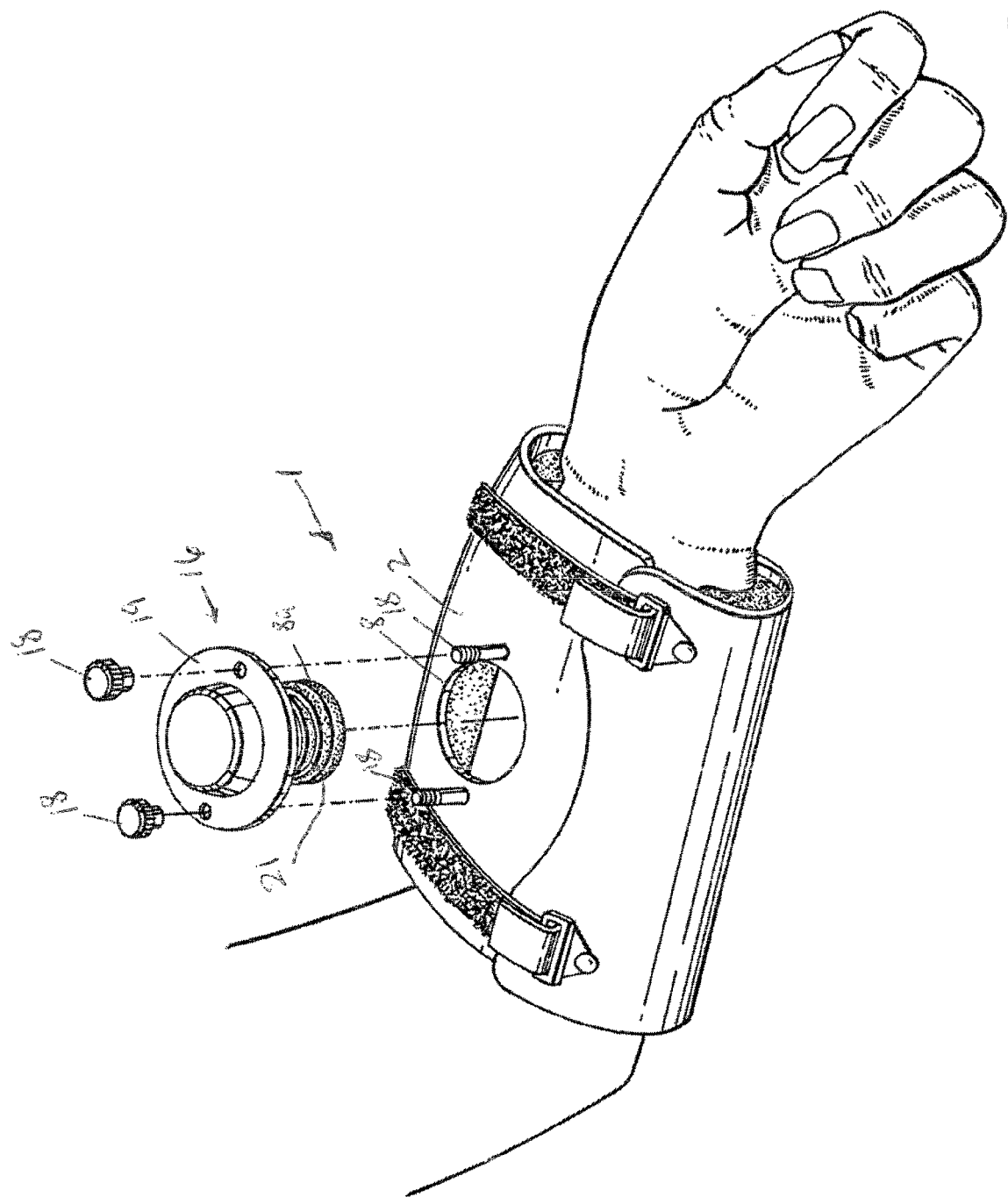

ORTHOPAEDIC DEVICE AND METHOD OF USE FOR TREATING BONE FRACTURES

FIELD OF THE INVENTION

The present disclosure is related generally to orthopaedic devices and methods of use thereof, for treating bone fractures.

BACKGROUND OF THE INVENTION

Currently known devices for applying pressure to soft tissue surrounding a bone fracture include a relatively soft material such as a sponge that is held against the soft tissue by a brace.

To use such devices, the sponge is positioned on the interior surface of the brace while the brace is in an untightened configuration so that when the cross-sectional dimension of the brace is reduced, the resulting position of the sponge overlies the apex of the bone fracture. In response to the reduction in diameter of the brace, a distribution of radially directed force is applied over the sponge and the sponge thereby applies a distributed pressure to the soft tissue adjacent to the bone fracture.

Such devices typically suffer from the drawback of requiring several iterations of engagement and disengagement of the brace to suitably adjust the magnitude of and the position at which pressure is applied to the soft tissue. Further, it is difficult to maintain the pressure applied to the soft tissue using such devices. Still further, the operation of such devices are complex and not user-friendly. Still further, they are limited to applying force to the soft tissues by mechanical means.

SUMMARY OF THE INVENTION

One embodiment of the invention includes an orthopaedic device for treating a bone fracture. The orthopaedic device has at least one pressure applying element configured to apply pressure to soft tissue adjacent to the bone fracture, and a holder configured to engage, in an engaged configuration, soft tissue adjacent to the bone fracture and, while in the engaged configuration, to facilitate adjustable positioning and securing of the at least one pressure applying element to the holder.

Another embodiment of the invention includes a method of treating a bone fracture with an orthopaedic device having a holder and one or more pressure applying element, the method comprising configuring the holder into an engaged configuration to engage soft tissue adjacent to the bone fracture, and while the holder is in the engaged configuration, adjustably positioning and securing at least one pressure applying element to the holder.

BRIEF DESCRIPTION OF THE FIGURES

FIG. 5 shows an embodiment of the orthopaedic device in an exploded view with two access ports and two foam pads.

FIG. 6 shows an embodiment of the orthopaedic device including a spring-loaded mechanism for applying a localized pressure to soft tissue surrounding a fracture.

DETAILED DESCRIPTION OF THE INVENTION

The present disclosure is related to orthopaedic devices having at least one pressure applying element configured to apply pressure to soft tissue adjacent to a bone fracture and a holder configured, in an engaged state, to engage the soft tissue adjacent to the bone fracture and, while in the engaged state, to permit adjustable positioning of the at least one pressure applying element to the holder. The present disclosure is further related to methods of use of the orthopaedic devices described herein to treat and align bone fractures and, in particular, for accelerating the healing of bone fractures and/or mitigating the pain associated with bone fractures, through mechanisms described in U.S. Pat. No. 5,171,310.

It is understood that soft tissue may include fat, muscle, facial tissue, small and large blood vessels, nerves lymphatic tissue and bone periosteum.

It is generally known that fracture healing is affected by three phenomena, mechanical pressure, electric and magnetic fields. Mechanically applied pressure alters the blood flow in the soft tissues. This changes the tissue pH and thus the concentration of free calcium ion is increased. Thus, increasing the pressure in the soft tissues results in an increase in the concentration of the free calcium ion. An electric field will result in an increase in the free calcium ion concentration by the application of an electrically induced force on the soft tissues. Additionally, an electrical field will impart a velocity to the free calcium ions. A magnetic field will also result in an increase in the free calcium ion concentration by the application of a magnetically induced force to the soft tissues while the magnetic field will impart a velocity to moving calcium ions. The present application describes devices and methods to apply one or more of the above phenomena to align an angulated fracture and to manipulate (increase) the concentration of the free calcium ions around the fracture site to accelerate its healing and mitigate pain.

Exemplary embodiments of the orthopaedic devices and methods of use thereof will be described with reference to the accompanying drawings.

First Embodiment

In a first embodiment, orthopaedic device 1, described below with reference to FIGS. 1-3, 5, 7A, 7B and 15-18, includes one or more pressure applying elements 16 and a holder 2.

The one or more pressure applying elements 16, to be described in detail below, is configured to be adjustably positioned on to the holder 2 and configured to adjustably apply pressure to the soft tissue adjacent to the bone fracture.

The holder 2 is configured to be positioned onto a target body part and to engage soft tissue adjacent to a bone fracture. It is understood that although the holder 2 is illustrated in the figures as a brace, the holder 2 may alternatively be a splint, a cast, a bandage, or a structural member that surrounds a body part, in whole or in part.

Figure 1:
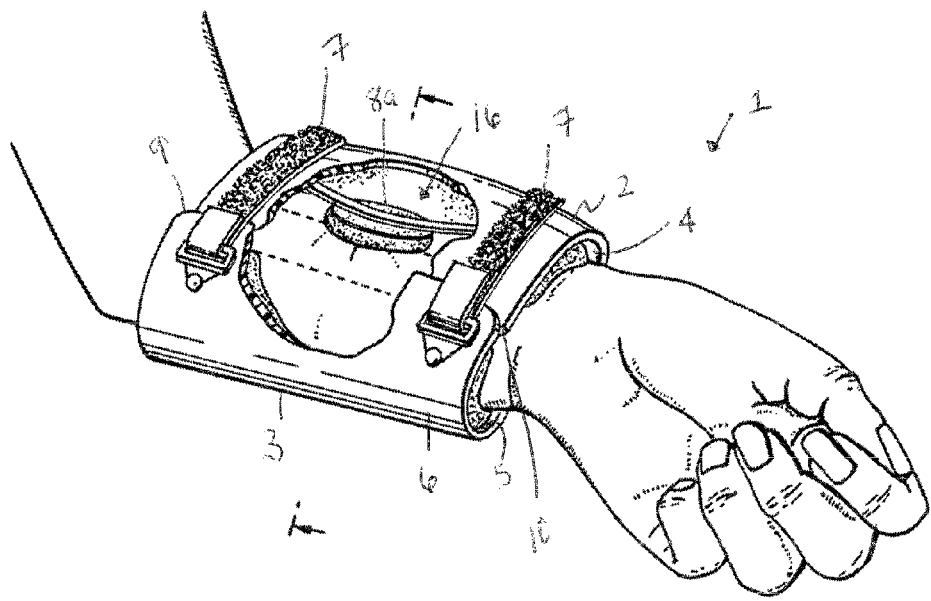
FIG. 1 shows an embodiment of the orthopaedic device that includes one access port.
Figure 2:
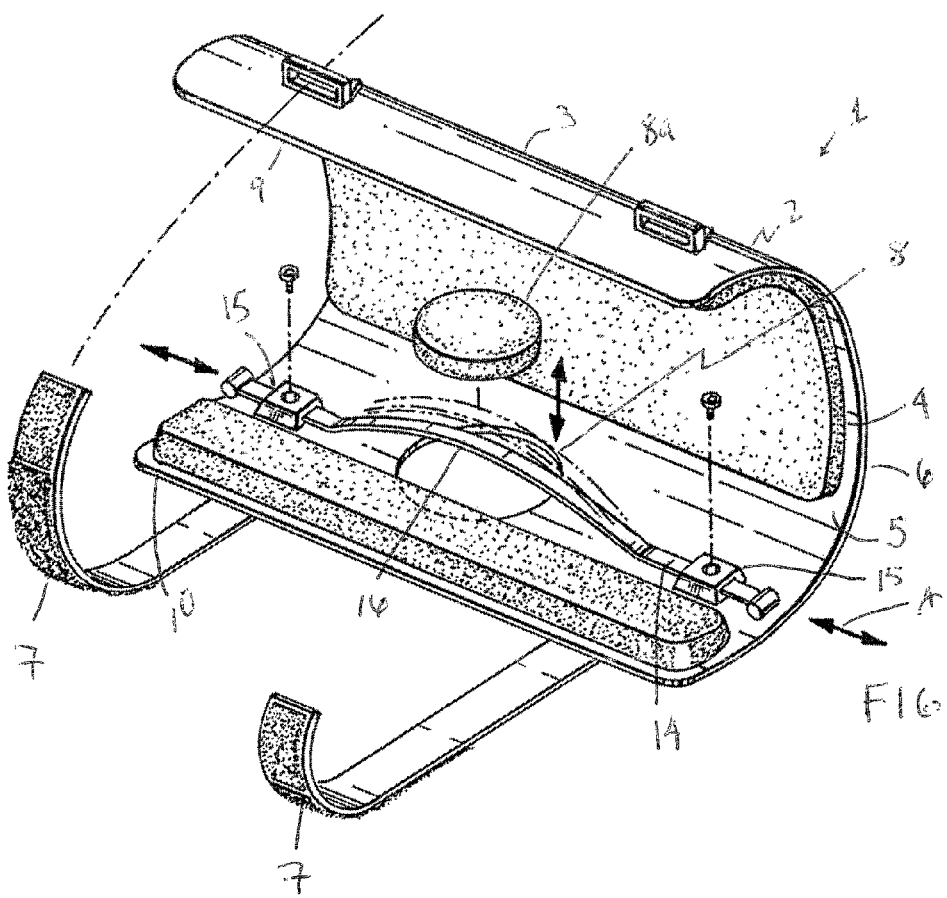
FIG. 2 shows an exploded view of the orthopaedic device of FIG. 1 with a foam pad.

As illustrated in FIGS. 1 and 2, the holder 2 has, for example, a formed open shell configuration along a longitudinal direction 3 that defines a first edge 9 and a second edge 10. The open shell configuration of the holder 2 further defines longitudinal openings 4 at a first and second end of the holder 2, as well as an inner surface 5 and an outer surface 6. The holder 2 is configured to be of a length and width for encircling a target body part in whole or in part therein. Further, the holder 2 is substantially rigid in the longitudinal direction 3 and is thus suited to laterally support the target body part and align an angulated fracture.

Figures 15, 16:
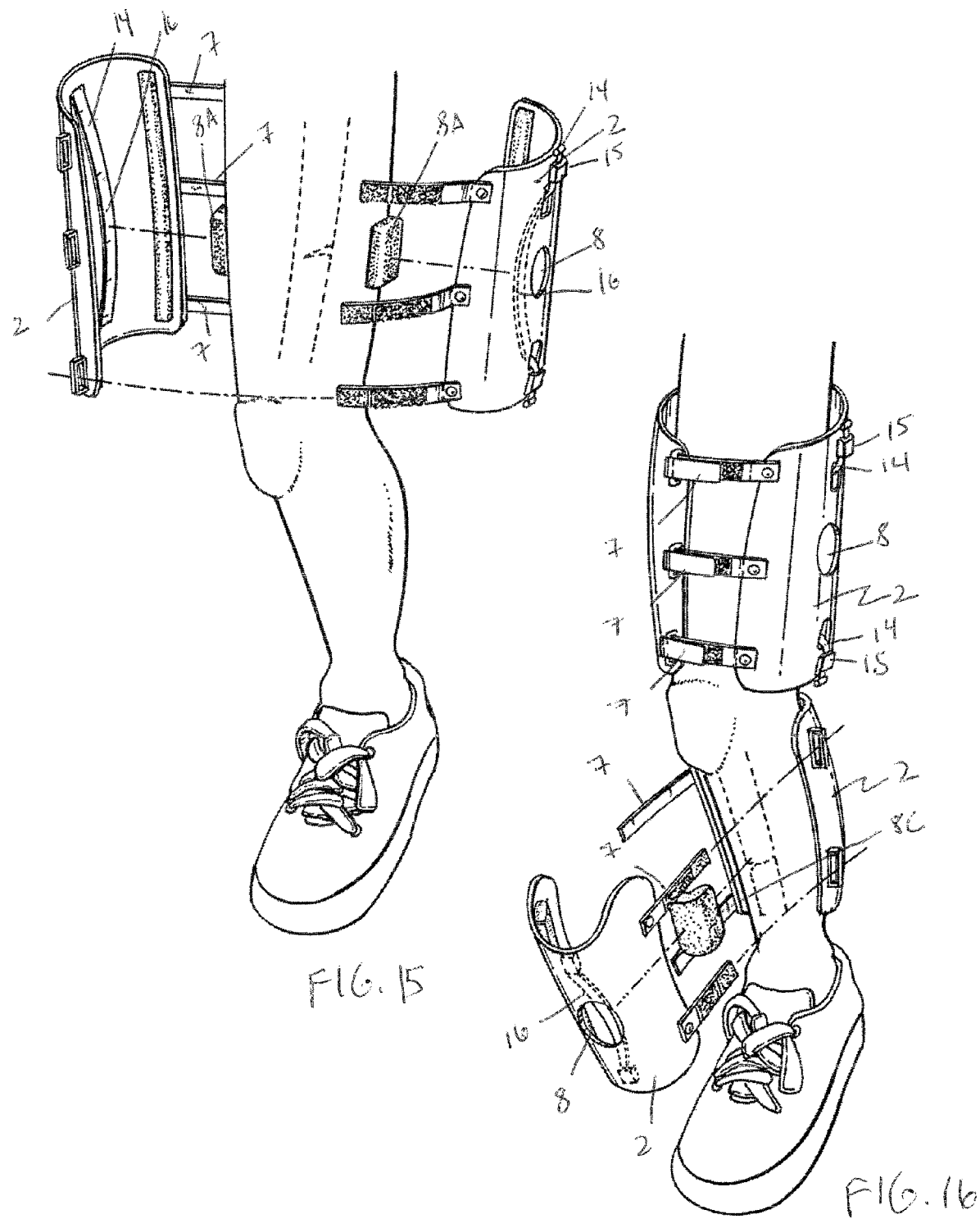
FIGS. 15 through 18 show the orthopaedic device being applied to a leg bone fracture with different holder configurations.

As illustrated in FIGS. 15 and 16, the holder 2 may be constructed with more than one formed open shell sections and/or annular sections so as to divide the holder 2 into two or more parts, which may be completely or partially separated. Where the holder 2 is composed of two or more parts, the parts can be configured such that, when engaged, the parts surround a target body part with one more bone fracture.

The holder 2 further includes a cross-sectional adjustment mechanism 7 including, for example, an adjustable strap wound through a loop, a loop and hook material such as VELCRO® (see FIGS. 1 and 2), a locking or clipping mechanism, a snap-fit, a button, a lacing, a zipper, or a ratcheted-type of mechanism, or any other type of mechanism known in the art.

The cross-section adjustment mechanism 7 can be operated to apply a hoop stress to holder 2 to reduce the cross-sectional dimension of the holder 2 to thereby fit and secure the holder 2 to the target body part. In this engaged state, the holder 2 is further configured to facilitate adjustably positioning the one or more pressure applying elements 16 to the holder 2 and to sustain the radially-directed pressure applied by the one or more pressure applying elements 16 to the soft tissue adjacent to the bone fracture.

In a first example of the orthopaedic device 1 of the present embodiment, the holder 2 includes an access port 8, which extends through (i.e., through the outer surface 6 and through the inner surface 5) of the holder 2. The access port 8 is configured to have a dimension suitable for permitting a pressure applying element 16 to operate therethrough or to be adjusted therethrough to position and apply a localized pressure onto soft tissue surrounding a bone fracture, either directly or through pressure applied to an intermediary contact material (described in further detail below) which then distributes the applied pressure onto the soft tissue.

The access port 8 facilitates adjustment of the pressure applying element 16 through the access port 8 so the holder 2 need not be removed once it is positioned and secured in an engaged state on a target soft tissue. As illustrated in FIGS. 1 and 2, the access port 8 in the orthopaedic device 1 allows pressure to be applied and suitably adjusted in a localized manner from outside the holder 2 through the access port 8 after the holder 2 has been fitted onto the target soft tissue.

The access port 8 disposed on the holder 2 can be of any suitable shape, which will permit a pressure applying element 16 to operate therethrough. FIG. 2 shows the access port 8 as being circular in shape, but this is meant to be merely exemplary. The access port 8 can be any suitable shape including, for example, oval, slot-shaped, square, rectangular or triangular.

The access port 8 renders the process of applying and adjusting a localized pressure onto soft tissue adjacent a bone fracture conveniently accessible to a user and/or healthcare professional. The pressure applying element 16 can be readily adjusted to maintain the pressure close to a set level. The pressure applying element 16 can also permit the user and/or healthcare professional to relieve the applied pressure in the event that the applied pressure exceeds a comfort level or other desired level.

Turning now to FIG. 5, in a second variation of the orthopaedic device 1, the holder 2 may contain a plurality of access ports 8. The plurality of access ports 8 is particularly beneficial for positioning one or more pressure applying elements 16 onto soft tissue of the affected body part. In particular, the plurality of access ports 8 can permit the selective use and/or adjustment of one or more pressure-applying elements 16 at different locations of the holder 2 as shown in FIG. 7A where a pattern of access ports 8 are shown as disposed over the holder 2.

With multiple access ports 8 located along the holder 2, the healthcare professional may surround the arm with the holder 2 having the multiple access ports 8 and then use one or more pressure-applying elements 16 to apply pressure where the healthcare professional desires it.

Figure 7A:
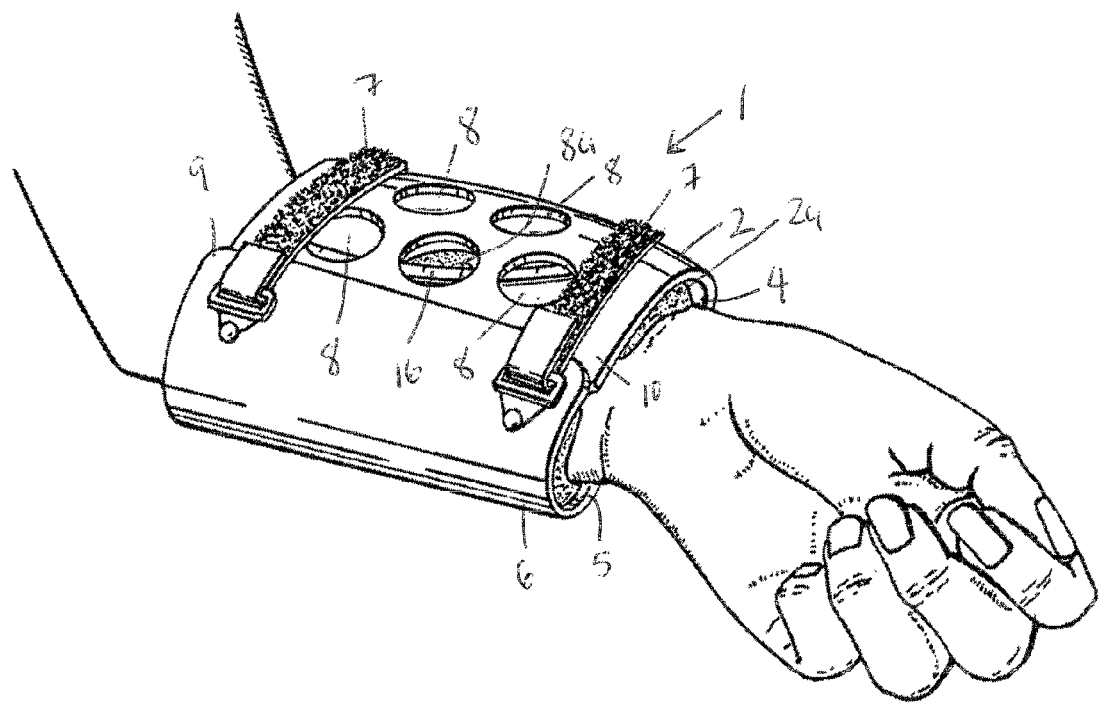
FIG. 7A shows an embodiment of the orthopaedic device with multiple access ports on the holder.

A uniform access port pattern such as the one shown in FIG. 7A is provided on the holder 2 to allow almost any soft tissue pressure application to be achieved by the use of appropriate pressure-applying elements 16. In this manner, the healthcare professional can have a holder 2 that includes multiple access ports 8 so the healthcare professional can first secure the holder 2 without requiring exact alignment of access ports 8 and use one or more pressure applying elements 16 to achieve the desired pressure application pattern over the fracture area.

Figure 7B:
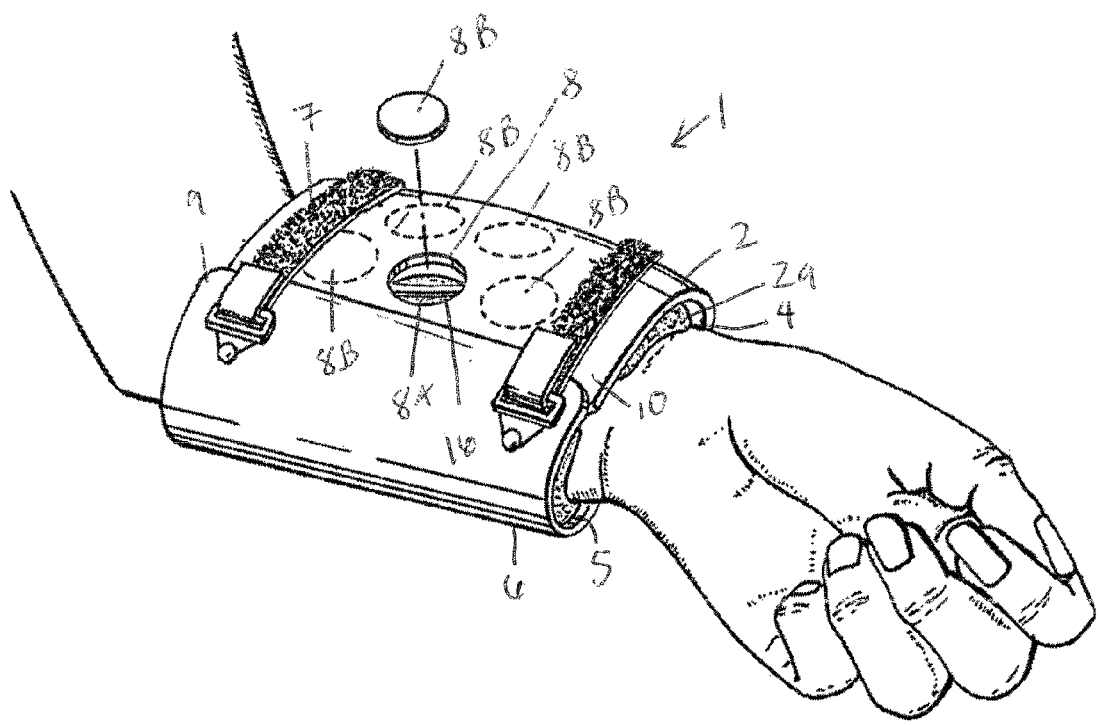
FIG. 7B shows an embodiment of the orthopaedic device with multiple covered access ports.

In FIG. 7A the access ports 8 are provided on the holder 2 in an opened configuration, however the present disclosure is not limited to this configuration, and the access ports 8 can be covered with a covering that is removable. In FIG. 7B, the provided access ports 8 are initially covered with removable coverings 8B. Accordingly, when the holder 2 is placed over the fracture, the healthcare professional may remove one of the coverings 8B to access the access port 8 beneath the covering 8B, and thus, introduce the pressure applying element 16 into the desired access port 8, and keep the remaining access ports 8 covered or closed.

In a third variation where a substantial amount of pressure is to be introduced over a specific portion of soft tissue, a group of pressure-applying elements 16 can be applied to extend into one access port 8 and to apply pressure to the particular portion of the soft tissue surrounding a bone fracture.

Figure 3:
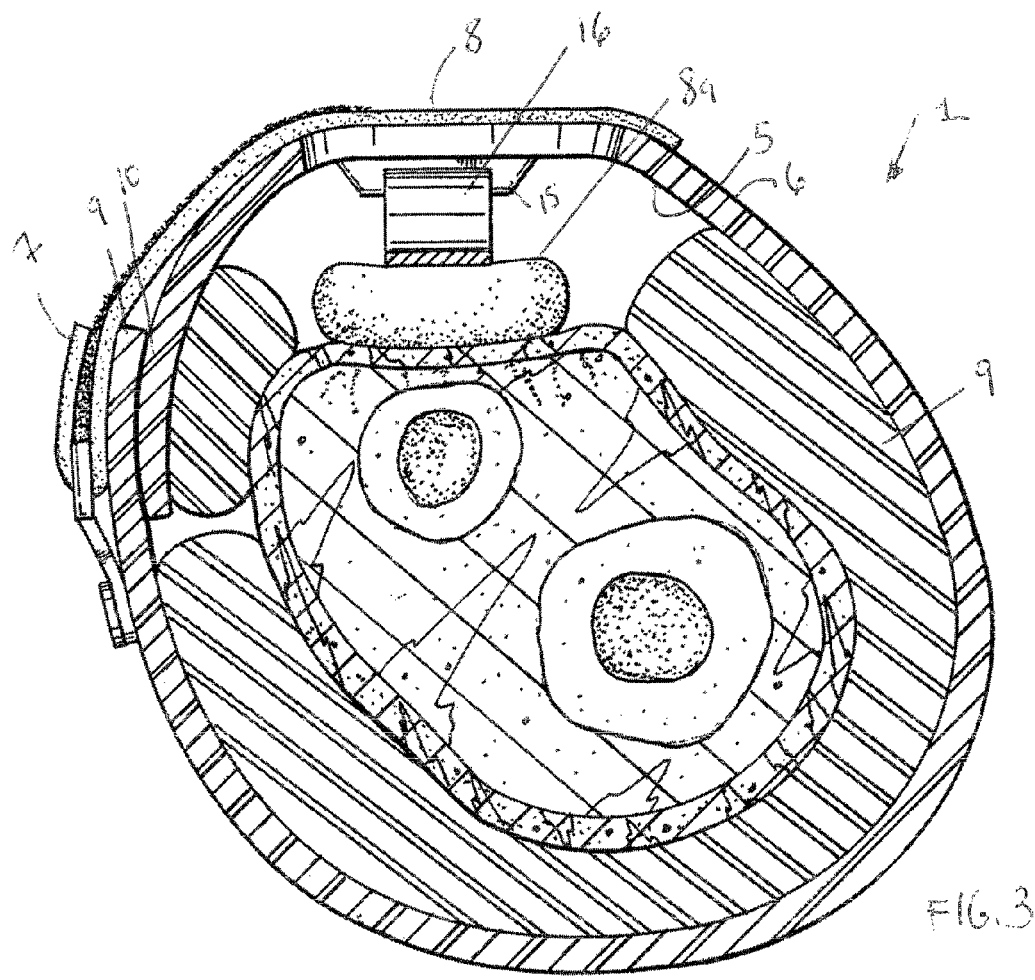
FIG. 3 shows a cross sectional view of the device of FIG. 1 applying pressure to the foam pad.

Turning now to FIG. 3, there is shown a cross sectional view of the orthopaedic device, and in particular, the pressure applying element 16 applying pressure to an intermediary contact material 8a, through the access port 8, according to a fourth variation of the present embodiment. In the orthopaedic device 1, an intermediary contact material 8a can be used to transmit the pressure asserted by the pressure applying element 16, and to distribute the pressure such that the soft tissue is not injured. The intermediary contact material 8a, which is inserted between the pressure-applying device 16 and the soft tissue, can be either detachably engaged or permanently attached to the pressure applying element 16 or the holder 2. The intermediary contact material 8a has a size and a construction that renders the pressure applying element 16 capable of transmitting and distributing the applied pressure onto the soft tissue. The pressure distribution can be either nearly uniform or non-uniform on the contacting soft tissue surfaces.

The intermediary contact material 8a can be constructed in whole or at least in part of, for example, foam, a polyurethane, rubber, plastic, silicone, or any deformable material or any combinations thereof. Furthermore, the intermediary contact material 8a may also contain hollow compartments.

The intermediary contact material 8a can be, for example, a disc-like foam pad, as illustrated in FIGS. 2, 3 and 5. Alternatively, a foam inner lining 2a arranged to the inner surface of the holder 2 can serve as an intermediary contact material 8a to minimize direct contact of the hard shell structure of holder 2 with soft tissue and to distribute pressure applied by the pressure applying element 16 onto the soft tissue.

The thickness of intermediary contact material 8a can be, dependent on the material of construction, from a few millimeters to 1-2 cm or more. For example, generally, a thicker intermediary contact material is used with an orthopaedic device applied to a larger limb in order achieve the desired pressure distribution.

In a fifth variation, the pressure applying element 16 or the intermediary contact material 8a may include radiographic markers (i.e., a radiographically dense material) that can function as markers in an x-ray image in order to reveal the position and angle of the pressure applying element 16 relative to the bone fracture. X-ray images can be taken to determine the positioning of the pressure application area relative to the fracture. Appropriate adjustments can then be made to achieve proper positioning of the pressure application area.

It should be appreciated that the configuration of orthopaedic device 1 and, in particular, holder 2 may vary depending on, for example, the type, location and specific geometry of the bone fracture.

Method of Use

The orthopaedic device 1 described in the first and subsequent embodiments can be used in any suitable manner according to methods understood in the healthcare profession to align and treat bone fractures such that the healing of a bone fracture can be improved and in particular, accelerated.

There are many factors which can determine how the orthopaedic device 1 is used. Such factors include, for example, the type of fracture and the location of the fracture in the body. As an example, for an angulated fracture, the orthopaedic device 1 can be configured to selectively apply localized pressure against the apex of the angulation in order to reduce the angulation over time while promoting healing of the bone. In contrast, for a non-angulated type of fracture, for example, one fixed with an intramedullary rod, the orthopaedic device 1 can be configured to apply one or multiple points of localized pressure at the same time or alternated over time for the biochemical effects.

Figure 17:
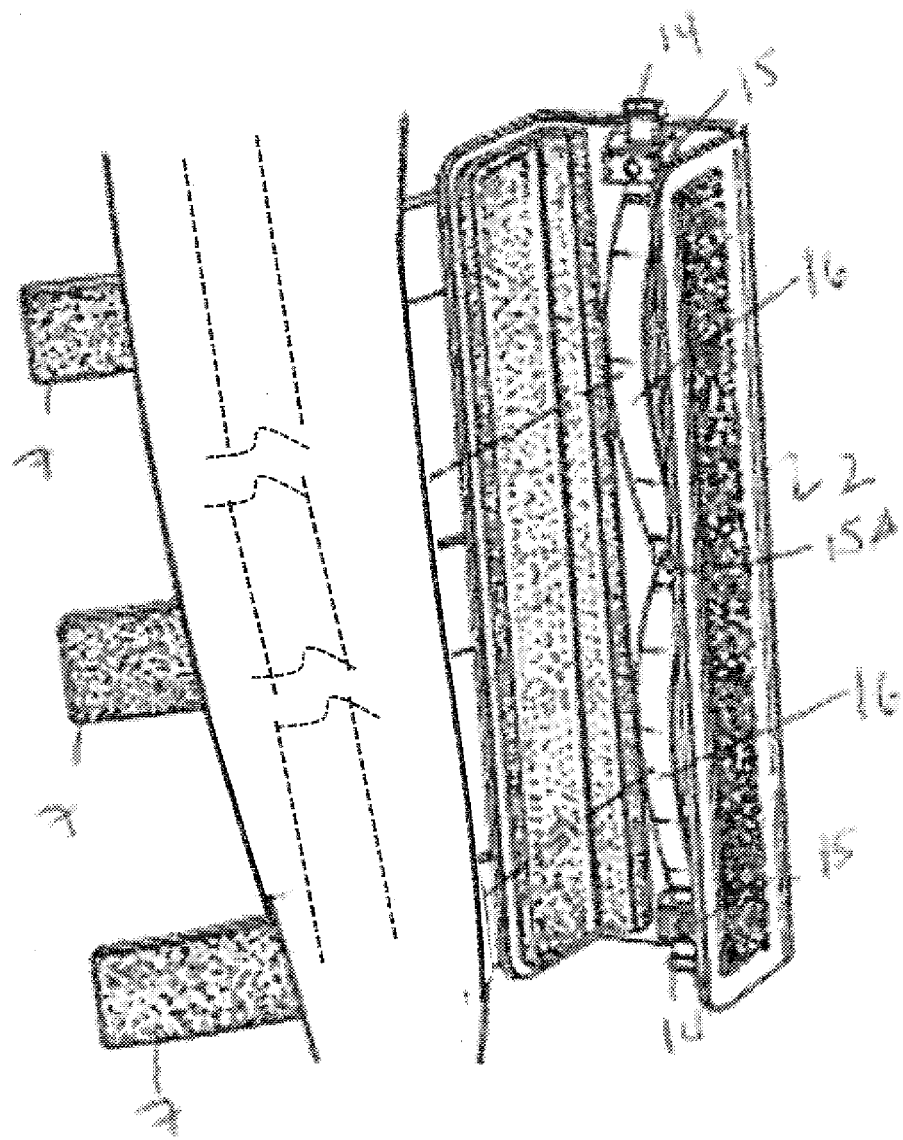

As illustrated in FIG. 17, the orthopaedic device 1 and, in particular, the holder 2 can be configured to treat a simple or segmental fractures (a single bone fractured in two different sites, simultaneously). The orthopaedic device 1, and in particular, the holder 2 can be configured to treat, for example, a complete fracture, incomplete fracture, linear fracture, transverse fracture, oblique fracture, segmental fracture, compression fracture, spiral fracture, stress fracture or other bone fractures with other geometry.

Figure 18:

It should also be appreciated that the orthopaedic device 1 and, in particular, the holder 2 can be configured to be of a size suitable for encircling, in whole or in part, any body part. As illustrated in FIG. 18, the orthopaedic device 1 and, in particular, the holder 2 can be configured to encircle body parts such as the torso in order to treat bone fractures in those parts of the body. Other bones of the body which can be treated by orthopaedic device 1 include, for example, the humerus, radius, ulna, femur, tibia, fibula, clavicle, spine, pelvis, carpus, metacarpals, metatarsals, phalanx (for both hand and foot), talus, calcaneus, patella, scapula, sternum, and rib bones. In addition, the orthopaedic device 1 and, in particular, the holder 2 can be configured over the fractured part, to allow the pressure-applying element 16 to be positioned in proximity to and to treat fractures located on a diaphyseal, metaphyseal, proximal or distal portion of a bone. In FIG. 18, the holder 2 is applied to the shoulder and strapped to the chest wall fixing it over the fractured clavicle. The access port 8a is then positioned over the fractured clavicle, allowing the pressure-applying element 16 to be positioned over the fracture.

It should also be appreciated that the orthopaedic device 1 can be used in connection with other support structures.

The pressure applied by a pressure applying element 16 against soft tissue can be any quantifiable amount of pressure that can accelerate the healing of a bone fracture. For example, the applied pressure can be sufficient to diminish local blood flow and thereby increase the local free calcium ion concentration in the blood in soft tissues adjacent to the bone fracture. In a first example, the applied pressure is anywhere within the range of about 20 to about 100 mm Hg, and more typically within the range of about 30 mm Hg to about 90 mm Hg. In a second example, the applied pressure is within the range of about 30 to about 50 mm Hg. In a third example, the applied pressure is within the range of about 60 to about 90 mm Hg. In a fourth example, the applied pressure is within the range of about 30 to about 40 mm Hg. It should be appreciated that various applied pressure values/ranges and distributions are within the scope of the present disclosure and the present disclosure is not limited to any specific pressure value/range.

The period of time that the applied pressure is retained on the soft tissue may be as long as several days or may be very short, e.g., even less than 0.5 minute, applied intermittently, for example in a pulse-like manner. For example, the period of time can be the full period of time that the orthopaedic device 1 is worn by the user or a portion of time that the orthopaedic device 1 is worn. The present orthopaedic device 1 allows the amount of pressure and the intervals of applied pressure to be readily adjusted by the user.

Second Embodiment

In a second embodiment, an orthopaedic device 1 includes a holder 2 and a mechanical pressure applying element 16. The mechanical pressure applying element 16 is supported by and/or connected to the holder 2 and is configured to apply and maintain a desired pressure directly against the soft tissue or indirectly against the soft tissue through an intermediary contact material 8a.

FIG. 2 illustrates a first example of a mechanical pressure applying element 16 comprising a strip 14 that is relatively flexible but inextensible. The mechanical pressure applying element 16 further comprises locking/unlocking elements 15 disposed on the holder 2 at positions adjacent to the access port 8 such that a length-adjustable portion of strip 14 spans across the access port 8. The length-adjustable portion of strip 14 that spans across the access port 8 can be manipulated by the user into a convex shape in a direction toward the soft tissue to apply pressure to the soft tissue. The strip 14 can be arranged on the outer surface 6 of the holder 2 and be manipulated by the user to protrude through the access port 8 to apply pressure to the soft tissue. Alternatively, the strip 14 can be arranged on the inner surface 5 of the holder 2 allowing the user to manipulate the strip 14 through the access port 8. Both configurations facilitate the positioning of strip 14 and setting a desired pressure without disengaging the holder 2 from the soft tissue. Once a desired pressure is set, the strip 14 can be locked in place using locking/unlocking elements 15 to maintain the desired pressure for a desired period of time. The locking/unlocking elements 15 can also be unlocked in order to rapidly disengage the strip 14 in the event of discomfort, malfunction or emergency.

The strip 14 can be of any suitable thickness and constructed of any suitable material, which will permit the strip 14 to deform in bending and apply and maintain a desired pressure for a desired time interval. For example, the strips 14 can be constructed of a suitable metal or metal alloy, which contains enough rigidity to maintain a pressure against the soft tissue, while possessing enough flexibility to bend and bulge toward the soft tissue. Some examples of suitable metals include iron-containing metals (e.g., steel), titanium, aluminum and alloys. The strip 14 can also be constructed of for example, a sufficiently flexible and inextensible plastic material or metal-plastic composite.

As illustrated in FIG. 5, in addition to the two locking/unlocking elements 15, the strip 14 may be fastened to holder 2 at one or more an additional points 15a. Such a configuration defines two length adjustable portions on the strip 14 that can be adjusted independently. Further, this configuration of strip 14 allows for selectively applying a localized pressure onto one or two regions of soft tissue by effectively bulging one or both length adjustable portions of the strip 14.

The strip 14 can be of a width which is less than or equal to or even larger than the diameter of the access port 8. Alternatively, two or more strips 14 can span across one or more access ports. Each of the multiple strips 14 can be individually and independently length-adjusted. Alternatively, the multiple strips 14 can be connected so that adjustment of one strip 14 can affect other strips 14. In such a configuration, the strips 14 are disposed in a parallel manner to form a width so that a smooth deforming surface (e.g., convex or biconvex) results.

Figure 4:
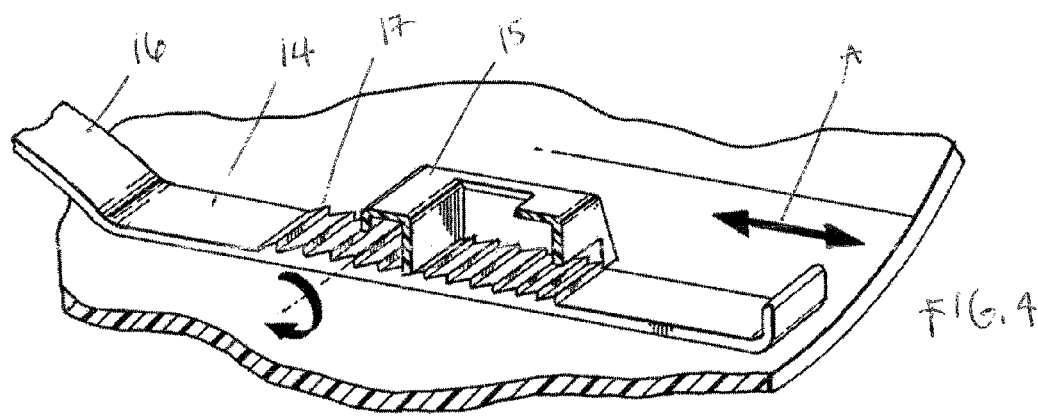
FIG. 4 shows a close up of a ratcheted strip.

In a second example, a mechanical pressure applying element 16 comprises a ratcheted strip 14, as illustrated in FIG. 4. The ratcheted strip 14 includes a number of ratcheting elements 17 that can be equally spaced from each other. The ratcheting elements 17 can be configured to engage with an interlocking receiving element 15 to secure the ratcheted strip 14 to apply a desired level of pressure to the soft tissue.

In a third example, a mechanical pressure applying element 16 comprises a load-adjustable spring element 21, which is operatively connected through an access port 8, between an intermediary contact material 8a, which further contacts the soft tissue, and a plate 19, which is located on another end of the load adjustable spring element 21 opposite from the intermediary contact material 8a, as illustrated in FIG. 6.

In FIG. 6, the plate 19 coupled to the load-adjustable spring element 21 is operatively connected to the holder 2 by a screw and nut mechanism 18 that can adjust the bias on the load-adjustable spring element 21. Tightening the nut of the mechanism 18 increases the load on the load-adjustable spring element 21. Loosening the nut of the mechanism 18 decreases the load onto the load-adjustable spring element 21. By increasing the load on the load-adjustable spring element 21, this spring state corresponds to an increased pressure on the soft tissue over the fracture, and decreasing the load on the load-adjustable spring element 21 corresponds to a decreased pressure on the soft tissue over the fracture. It should be appreciated that instead of a load-adjustable spring element 21, another deformable element may be used. Alternatively, the body of the mechanical pressure applying element 16 may be formed with threads and be screwed directly to the access hole 8 which is provided with matching threads to receive the element 16, thereby avoiding the need for the screw and nut mechanism 18.

The load-adjustable spring element 21 described above can also be operatively coupled to other pressure applying elements. For example, load-adjustable spring element 21 can be operatively coupled to a strip 14. By adjusting the screw and nut mechanism 18, the plate 19 can be moved to compress the load-adjustable spring element 21 against one or more strip 14 through an access port 8. When the desired pressure is attained, the strip 14 can be locked in place with locking/unlocking element 15 to maintain the applied pressure.

In a fourth example, the adjustable pressure applying element 16 comprises a bladder 8C containing a liquid, gas or a solidifiable liquid.

Figure 14:
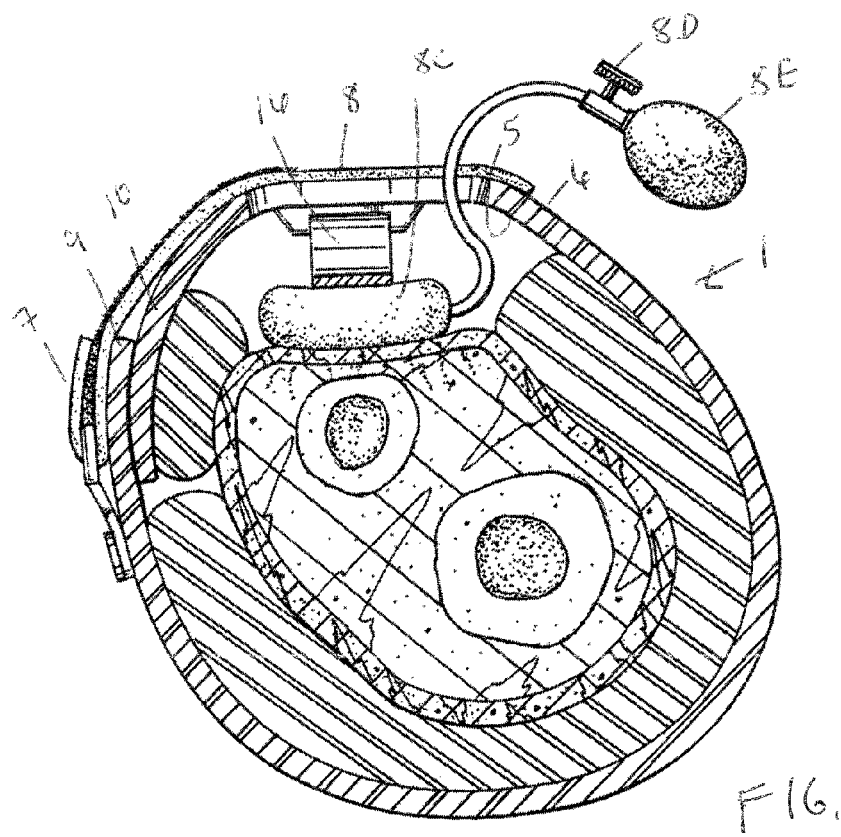

As illustrated in FIG. 14, the bladder 8C can be connected to a valve 8D to introduce air (gas) or liquid via pump 8E, and can be supported with or connected to the inner surface 5 of the holder 2. The use of air (gas) in a relatively elastically expandable bladder 8C allows for the maintenance of a relatively uniform and constant pressure over the soft tissue. The bladder 8C can also be configured to be accessible through an access port 8. The fluid-filled bladder 8C is capable of being shaped, i.e., molded in form, through the access port 8 to protrude toward the soft tissue.

Figure 13:
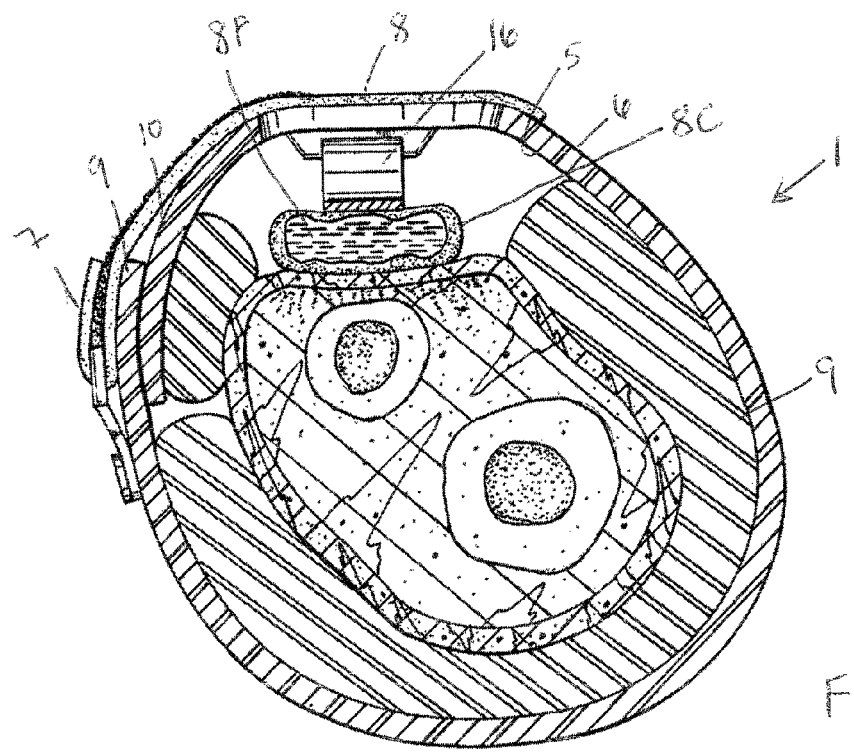
FIGS. 13 and 14 show cross sectional views of two embodiments of the orthopaedic device including adjustable fluid or gas filled bladders.

FIG. 13 shows a solidifiable liquid 8F introduced into bladder 8C. Upon establishing a desired pressure within bladder 8C against the soft tissue, the solidifiable liquid 8F is capable of changing into a rigid solidified form within a short period of time (e.g., in less than 1 minute).

The solidifiable liquid 8F can be any liquid known in the art capable of solidifying at room temperature in response to a stimulus. The stimulus can be, for example, a mixture of two portions of a mixture to commence a chemical reaction, which changes the solidifiable liquid 8F into a solid. The solidifiable liquid 8F should be capable of maintaining a rigid solid form either after removal of the stimulus or by intermittent or continued application of the stimulus. Alternatively, the stimulus can be an electrical charge or magnetic field supplied to a mixture to solidify the mixture.

The solidifiable liquid 8F can be, for example, a magnetorheological fluid. A magnetorheological (MR) fluid 8F is a type of fluid, which is converted to a highly viscous form or solid when stimulated by a magnetic field of appropriate strength. A MR fluid 8F is typically composed of micrometer or nanometer-sized magnetic particles (paramagnetic colloidal particles) suspended in a viscous medium, such as oil. The particles can be, for example, of an iron or magnetic iron oxide composition.

The disclosure also contemplates adjusting the magnetic field strength in order to vary the rigidity of the solidifiable fluid 8F in bladder 8C such that during exercise the pressure transmitted by the bladder 8C onto the soft tissue can be varied. Since a MR fluid requires the use of a magnetic field, the orthopaedic device 1 may also include a device in the holder 2 for providing a magnetic field. For example, appropriately sized electromagnetic coils can be included for this purpose.

Alternatively, the solidifiable liquid 8F can be an electrorheological fluid. An electrorheological (ER) fluid is a type of fluid which is converted to a highly viscous form or solid when stimulated by an electrical field (typically several kV/mm). An electrorheological fluid is typically composed of fine non-conducting (dielectric) particles (e.g., up to 50 microns in diameter) in an electrically insulating fluid. An example of an ER fluid 8F is corn flour suspended in an oil, such as a vegetable oil or silicone oil. The ER fluid 8F considered herein also include the more recent giant electrorheological (GER) fluids, which are typically able to sustain higher yield strengths at lower electrical fields. An example of a GER fluid 8F is a composition containing urea-coated nanoparticles of barium titanium oxalate suspended in silicone oil. The disclosure also contemplates adjusting the electric field strength in order to vary the rigidity of the solidifiable fluid 8F in bladder 8C such that during exercise the pressure transmitted by the bladder 8C onto the soft tissue can be varied. Since an ER fluid 8F requires the use of an electric field, the disclosure also contemplates including a device in the holder 2 for providing an electric field. For example, appropriately sized electrodes (charged plates) along with an electrical power source can be included for this purpose.

It should be appreciated that other mechanical pressure applying elements 16 can be used with the present disclosure. The above described embodiments are advantageous in that the pressure applied to the soft tissue can be adjusted and maintained without requiring removal or disengagement of the holder 2 from the body part.

Third Embodiment

A third embodiment is described below with reference to FIGS. 8-10.

Figure 8:
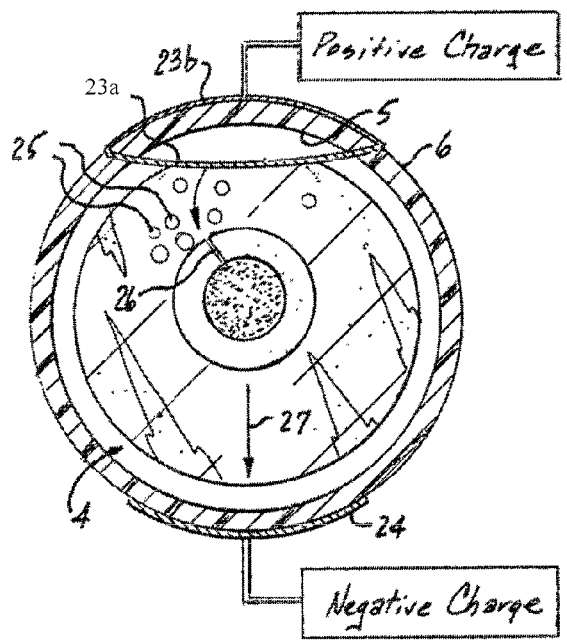
FIGS. 8-10 show three embodiments of the orthopaedic device containing capacitive coupling devices capable of applying two separate localized deforming pressure on soft tissue adjacent to a bone fracture.

FIG. 8 illustrates a cross-sectional view of an orthopaedic device 1 that includes a capacitive coupling device as a pressure applying element 16 for applying a soft tissue deforming pressure onto soft tissue adjacent to a bone fracture to treat and accelerate healing of the fracture.

The capacitive coupling device includes a first electrically-conductive foil element 23, having two foil portions 23a and 23b, and a second electrically-conductive foil element 24 that are positioned approximately opposite to each other on a holder 2. Foil elements 23 and 24 can be positioned or secured to the holder 2, for example, through access ports 8, such that a user can designate the positions of the foil elements 23, 24 on the holder 2 after the holder 2 is engaged to the soft tissue adjacent to the bone fracture.

The foil elements 23, 24 are electrodes and are designed such that foil elements 23, 24 can assume an electrical charge with portions 23a, 23b being positive and foil element 24 being negative.

The foil portions 23a and 23b are electrically interconnected to one another and contain the same charge. The foil portions 23a and 23b include a positive charge and thus repel from one another. The portion 23b is configured to be connected to the holder 2 to remain stationary, thereby allowing the portion 23a to repel away from portion 23b and to apply a pressure onto soft tissue when the portions 23a and 23b are charged.

The foil portion 23a can optionally contact an intermediary contact material to distribute the pressure applied by the foil portion 23 to the soft tissue adjacent to the bone fracture.

By modulating the electrical charge between the foil elements 23a and 23b, the amount of deflection of the foil portion 23a can be adjusted. Preferably, the foil portions 23a, 23b can be coupled to a controller (not shown) to permit the user to regulate the current passing through the foil portions 23a, 23b, and thus further adjust the amount of pressure on the fracture. For example, the controller can regulate the current passing through the foil portions 23a, 23b in an on-off pattern or other intermittent profile pattern of choice.

The foil portions 23a, 23b are constructed of any conductive material known in the art. Specifically, the foil portions 23a, 23b are constructed of resilient material which can apply and hold a suitable soft tissue deforming force on the fracture. Some examples of suitable materials for the foil portions 23a, 23b include various conductive metals (e.g., copper, silver, iron, and alloys or layered structures), and conductive polymers or plastics.

Figure 9:
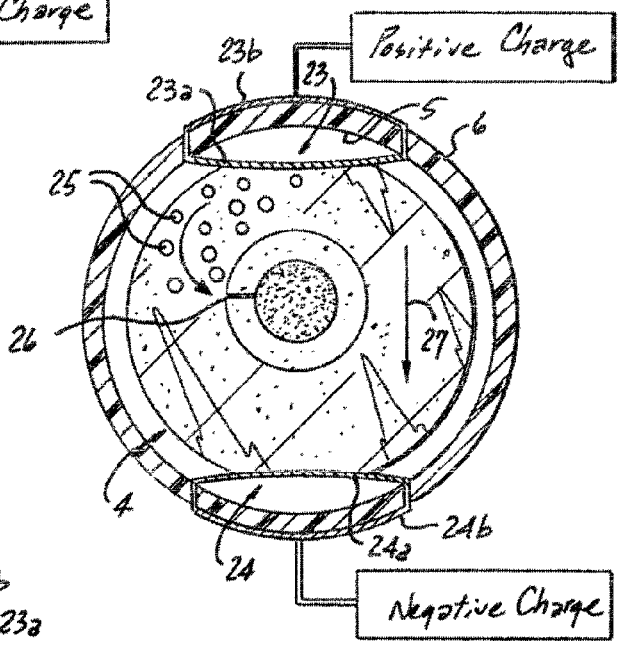

Alternatively, the foil portions 23a and 23b of like charge are not split from a common electrode as described in FIG. 8, but rather can be alternatively formed from two separate foil electrode 23a and 23b of like charge, with one foil electrode 23b attached to the inner surface 5 of the holder 2 and another electrode 23a being spaced away and in contact with the soft tissue and fracture to apply pressure to the fracture as shown in FIG. 9. The two separate foil electrodes 23a and 23b can be made to assume the same charge by, for example being connected to the same terminal of a battery, or by being connected to terminals of different batteries wherein the different terminals are of the same polarity.

The above described configuration of foil elements 23, 24 provides an additional benefit of directing calcium ions 25 toward the bone fracture by charge repulsion. In the above described configuration, an electrical potential 27 is created between foil elements 23, 24 such that calcium ions are directed away from the positive charged foil element 23 toward the negatively charged foil element 24. By positioning the deforming foil portion 23a against the fracture side of a bone, the calcium ions are directed toward, and thus concentrated at, the fracture site.

Turning now to FIG. 9, there is shown an alternative embodiment of the present disclosure wherein foil elements 23, 24 are positioned on a holder 2, with each foil element 23, 24 having two foil portions 23a, 23b, 24a, 24b, respectively. In this configuration, pressure can be applied at two regions of the soft tissue adjacent to the bone fracture from approximately opposite directions. This configuration may be advantageous in the instance whereby a fracture includes a specific geometry, and whereby the pressure and the electric field is applied to the body part from at least two different directions and can be adjusted to the desired level, independently.

Figure 10:
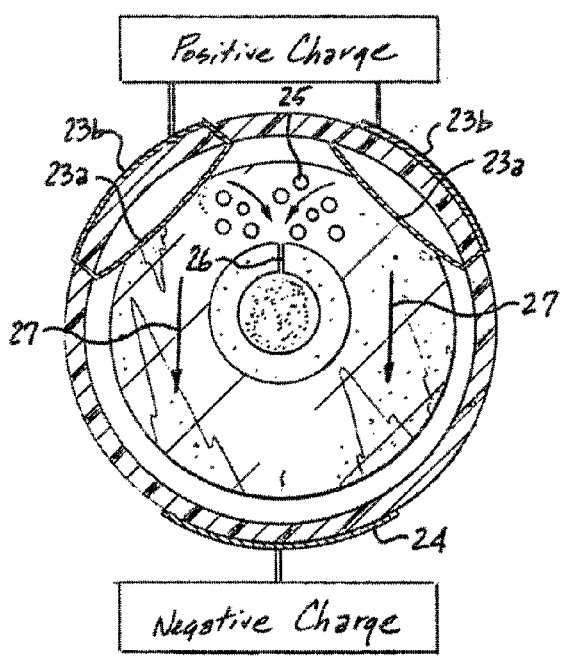

Turning now to FIG. 10, in an alternative variation, a plurality of positively charged foil elements 23, each having a pair of interconnected foil portions is arranged on a holder 2 relative to a negatively charged foil element 24. Such a configuration provides the orthopaedic device 1 with the ability to apply localized pressure simultaneously or alternately in at least two or more different locations of the soft tissue adjacent to the fracture for complex fracture shapes to accelerate healing of the fracture.

In another variation, the applied pressure can be modulated by the charge supplied to the desired foil elements 23a, 23b, 24, which modulates the field strength developed in the body part between the charged foil elements 23a, 23b, 24. For example, increasing a voltage between opposing foil elements 23a, 23b and 24 can increase the amount of applied pressure while decreasing a voltage between opposing foil elements 23a, 23b, and 24 can decrease the amount of applied pressure. Various amounts of charging can be supplied to the electrode foil elements and various charging configurations are possible and are within the scope of the present disclosure. Various charging patterns, including intermittent charging patterns, are therefore possible to apply to achieve various applied pressure levels and/or electric field strength levels and all such patterns are within the scope of the present disclosure.

The amount of voltage necessary to produce a sufficient level of charge in foil elements 23a, 23b, and 24 in order to produce a desired amount of localized pressure can all be readily calculated. For example, if the desired pressure (P) is known, the corresponding force (F) can be calculated by multiplying P by the area of contact of the contacting foil element 23a, 23b. Since F is the sum of the repulsive force $F_1$ (i.e., between 23a and 23b) and the attractive force $F_2$ (i.e., between 23b and 24), $F_1$ and $F_2$ can be adjusted to arrive at the desired F. Coulomb's Law can be used to calculate the appropriate levels of charge required to adjust $F_1$ and $F_2$ in order to achieve a desired F. For example, by Coulomb's Law:

$F_1 = \frac{1}{4}\pi \in_0 (q_1 \times q_2 / r_{12}^2)$ for the repulsive force, wherein $r_{12}$ is the distance between diverted foil elements 23a and 23b, and $q_1$ and $q_2$ are the amounts of charge on each respective foil element 23a and 23b; and $F_2 = \frac{1}{4}\pi \in_0 (q_2 \times q_3 / r_{23}^2)$ for the attractive force, wherein $r_{23}$ is the distance between diverted foil elements 23b and 24, and $q_2$ and $q_3$ are the amounts of charge on each respective foil element 23b and 24.

Using the above equations, appropriate charging values $q_1$, $q_2$, and $q_3$ can be found in order to provide a force F that can provide a pressure P. The charging values can be realized by selection of an appropriate voltage, wherein the optimal voltage can be calculated. Alternatively, the voltage necessary to produce a given soft-tissue deforming pressure can be found experimentally by observing the amount of pressure applied per amount of voltage.

The orthopaedic device 1 can include any suitable device for applying a voltage onto the foil elements 23a, 23b and 24. For example, the orthopaedic device can include a suitable electrical charging device, such as provided by a lithium-ion rechargeable battery, a plug in electrical connection, a nickel hydride battery, a renewable source, like a solar cell or another electrical source, such as a small electrical generator with a stator and rotor. The orthopaedic device 1 can also include battery connection ports and conductive leads (not shown).

Fourth Embodiment

A fourth embodiment is of orthopaedic device 1 comprising a holder 2 and a magnetic device as pressure applying element 16 connected to the holder 2 for applying a soft-tissue deforming pressure onto soft tissue adjacent to a bone fracture is described below with reference to FIG. 11.

The magnetic device includes a magnetic source 28 operating (e.g., attached) on a first side of the holder 2 and a flexible permanent magnetic strip element 29 associated with the magnetic source 28 positioned through an access port onto the holder 2.

In one configuration, the magnetic source 28 is an electromagnetic coil coupled to a power supply. The magnetic source 28 is capable of producing an adjustable magnetic field by modulation of the applied current to the electromagnetic coil. The flexible permanent magnetic strip element 29 is positioned through an access port on to the holder 2 and is operatively connected, for example, to the inner surface 5 of the holder 2 such that at least a portion of the permanent magnetic strip element 29 can protrude toward and apply pressure to a region of the soft tissue adjacent to the bone fracture when the magnetic source 28 is activated. The flexible permanent magnetic strip element 29 can be attracted or repulsed toward the soft tissue by inducing a magnetic field from the magnetic source 28, which can be the same polarity as the side of the flexible permanent magnetic strip element 29 facing the magnetic source 28. The like magnetic polarities may repel each other and cause the flexible permanent magnetic strip element 29 to protrude toward the body part, or alternatively, the opposite magnetic polarities can cause the flexible permanent magnetic strip 29 to move away from the fracture to reduce the applied pressure to the soft tissues surrounding the fracture.

It should be appreciated that an intermediary contact material (ex. foam pad 8a) can be positioned between the soft tissue and the flexible permanent magnetic strip 29 to distribute force to the soft tissue.

The flexible permanent magnetic strip 29 is constructed of any material, which is permanently magnetic, and of a suitable resilient construction (including thickness and composition) which renders the flexible permanent magnetic strip 29 capable of applying and holding a suitable soft-tissue deforming force. Some examples of suitable materials for the magnetic strip 29 includes any of the magnetic compositions known in the art (e.g., magnetite, cobalt, nickel, ceramic magnets, alnico, ticonal, rare earth magnets (e.g., samarium-cobalt and neodymium-iron-boron (NIB) magnets), combinations thereof, coatings thereof, and layered and non-layered composites thereof.

Figure 12:
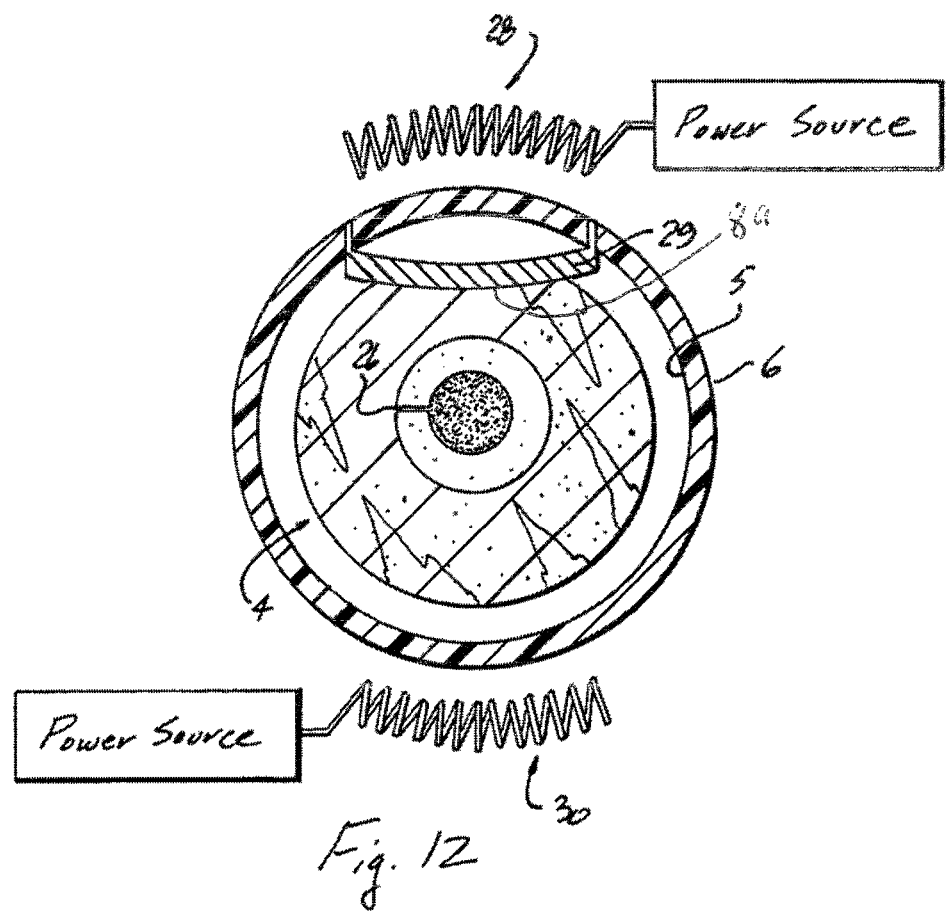

Turning now to FIG. 12, there is shown an alternative configuration with at least two magnetic sources 28, 30 to manipulate and adjust the amount of pressure the flexible permanent magnetic strip 29 applies to the soft tissue adjacent to the bone fracture. The second magnetic source 30 is disposed substantially opposite the first magnetic source 28. It should be appreciated that this positioning is illustrative and may change depending on the orientation of the fracture. The second magnetic source 30 operates on a second side of the holder 2 and approximately opposite to the first side; however, the magnetic sources 28 and 30 may be placed in any desired location relative to the fracture. Each of the first and second magnetic sources 28 and 30 produce magnetic fields. The two magnetic sources 28 and 30 work together to promote the bulging of the flexible magnetic strip 29 to apply pressure to the soft tissue and the fracture. Specifically, the switchable magnetic source 28 repels the flexible magnetic strip 29, while the switchable magnetic source 30 attracts the flexible magnetic strip 29.

Figure 11:
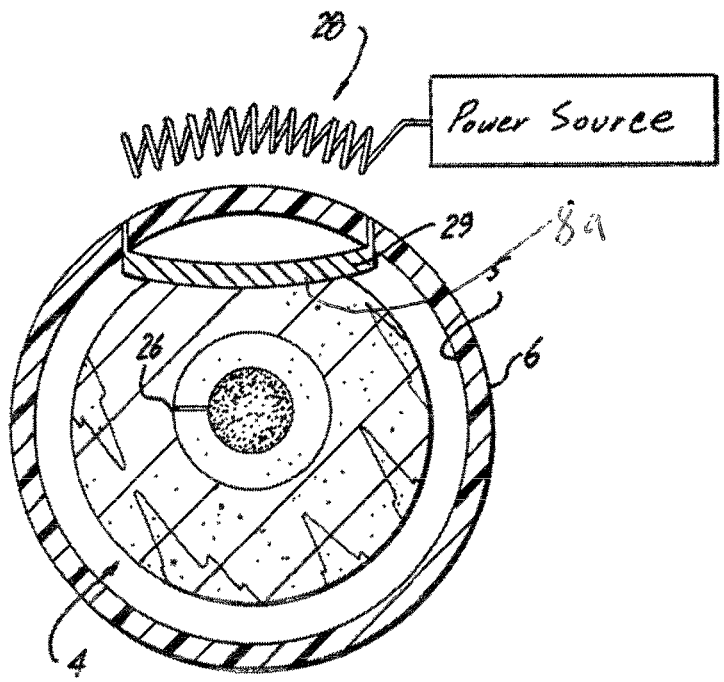
FIGS. 11 and 12 show two embodiments of the orthopaedic device containing magnetic coupling devices capable of applying a localized deforming pressure on soft tissue adjacent to a bone fracture.

It should be appreciated that the orthopaedic device 1 is not limited to a single magnetic strip 29 as show in FIGS. 11 and 12, and may have at least two strips 29. The number of magnetic strips 29 may depend on the fracture and geometry of the fracture. It should also be appreciated that the magnetic strip 29 is not limiting to one bending or bulging curved portion that contacts the tissue but depending on the polarity, the magnetic strip 29 can have more than one bulging or more than one curved surface. For example, a magnetic strip 29 can be connected to the concave inner surface 5 of the holder 2 in more than two locations such that more than one bulging section on the strip 29 can result. The holder 2 can apply localized pressure simultaneously or in different locations of the body part adjacent to the fracture to accelerate the healing. For example, the pressure can be adjusted by the selective operation of the magnetic sources 28, 30 by modulating the magnetic field or the current supplied to the coil.

The applied pressure is modulated by the magnetic field strength applied onto the flexible magnetic strip 29. For example, increasing the magnetic field strength can increase the amount of applied pressure, while decreasing the magnetic field strength can decrease the amount of applied pressure. The intensity of the magnetic field necessary to produce a sufficient attractive/repulsive force between the desired coil 28 or 30 and the magnetic strip 29 can be changed to produce a desired amount of pressure. Various magnetic field strength patterns, including intermittent charging patterns, are therefore possible to apply to achieve various applied pressure levels and/or magnetic field strength levels and are within the scope of the present disclosure.

A benefit of the magnetic field produced by the sources 28 or 30 is the ability to favorably influence calcium ions at the fracture site. For example, a magnetic field will concentrate the calcium ions in the compressed region because they are deflected by the magnetic field toward the fracture site. Such a magnetic field causes the calcium ions flowing in blood vessels near the fracture to follow circular paths of radius r=mv/qB, where m is the mass of the calcium ion, V is its velocity, q is its charge, and B is the applied magnetic field. By manipulating the intensity of the magnetic field, the trajectory of the calcium ions can be manipulated to congregate in the blood vessels surrounding the fracture. Because the flexible magnetic strip element 29 is intimate with soft tissues over the fracture, this effect is maximized. This increased concentration of calcium ions will further accelerate healing of the fracture.

The amount of magnetic field strength necessary to produce a suitable deforming force may depend on the size and construction of the flexible magnetic strip 29 as well as other factors. For example, if the desired pressure (P) is known, the corresponding force (F) can be calculated by multiplying P by the area of contact of the flexible magnetic strip 29. Since F is the sum of the repulsive force $F_1$ (i.e., between 28 and 29) and the attractive force $F_2$ (i.e., between 29 and 30), $F_1$ and $F_2$ can be adjusted to arrive at the desired F. To calculate the appropriate magnetic field required to adjust $F_1$ and $F_2$ in order to achieve a desired F, the equation $F=A*B^2/2*\mu°$ can be used, wherein F is force in Newtons, A is the surface area of the mat and coil in meter$^2$, B is the strength of the magnetic field in weber/meter$^2$, and $\mu°$ is the magnetic permeability constant. For example, to apply about 30 mm Hg pressure (about 400 dyne/cm) to the soft tissues by a 10 cm by 10 cm magnetic strip 29, a magnetic field of 0.01 weber/meter$^2$ (i.e., approximately 100 Gauss) can be used. When there is separation of the magnet source of length L by distance x, the Force F can be represented as $F=B^{2*}A^2(L^2+R^2)/\Pi\mu°L^2[1/x^2-1/(x+2L)^2-2/(x+L)^2]$ wherein R is the radius of the magnet or coil 28. Various coil 28, 30 and magnetic strip 29 size configurations are possible and within the scope of the present disclosure.

The orthopaedic device 1 can include a suitable electrical power supply for creating a magnetic field in the electromagnetic coils 28 and 30. For example, the orthopaedic device 1 can include a battery or other electrical source for this purpose, such as a photovoltaic solar cell, a capacitor, an ultracapacitor, a lithium ion battery, a nickel hydride battery, an electric generator including a rotor and a stator or a plug for coupling the electromagnetic coils 28 and 30 to an electrical household power supply line.

The orthopaedic device 1 can also include features (not shown) for connecting the power supply with the holder 2 and the magnetic device 28 and 30. In one configuration, at least one of the magnetic sources 28 and 30 and the permanent magnetic strip element 29 are detachably engaged with the holder 2 using a suitable detachable connector, such as, a clip, a removable connector engaged in an engageable slot or groove located in or on the holder 2. In another configuration, at least one of the magnetic sources 28 and 30, and the permanent magnetic strip element 29 can be fixedly attached to the holder 2. An intermediary contact material can be connected to the permanent magnetic strip element 29 or may be placed between the soft tissue and the permanent magnetic strip element 29 to distribute the pressure along the soft tissue and fracture to accelerate the healing.

Fifth Embodiment

The holder 2 may further include a pressure indicator to provide a quantifiable indication of the pressure being applied to the soft tissue and the fracture. The pressure indicator (not shown) may provide an indication to a user that a suitable pressure has been achieved to accelerate the healing of the fracture or when a desired pressure against soft tissue has been reached, or alternatively that the pressure should be increased/reduced.

In one configuration of the pressure indicator, an auditory indicator can sound to indicate that the desired pressure has been reached.

In another configuration of the pressure indicator, a visual-based indicator can display, for example, numbers, colors, or both, to indicate a certain degree of applied pressure. The visual-based indicator is based on a mechanism whereby as the strip 14 is pressed down to exert pressure to the surface of the body the force exerted on the locking ends 15 would be utilized to indicate the pressure applied to the body surface. This can be accomplished, for example, by attaching at least one of the locking ends to the holder 2 by a relatively stiff spring. The extension/contraction of the spring will then indicate the amount of force being transferred to the holder 2, thereby the pressure exerted to the body surface. A coloring or marking means can also be used as a scale to indicate the level of pressure applied to the body surface.

In another configuration, a similar type of mechanism is applied to a spring element 21 described above with regard to FIG. 6, wherein a flexible strip with pressure-indicating marks is overlaid onto or connected to the spring element 21. The compression and expansion of the spring element 21 causes the pressure-indicating flexible strip (not shown) to move in a like manner. A pressure-indicating mark on the flexible strip, when visible, thus indicates the applied pressure for a given compression of the spring element 21.

In yet another configuration, the visual-based indicator can operate by use of a material or combination of materials, which exhibit a change in color when a pressure change occurs. Various indicator configurations are possible and within the scope of the present disclosure.

Sixth Embodiment

Figure 19:
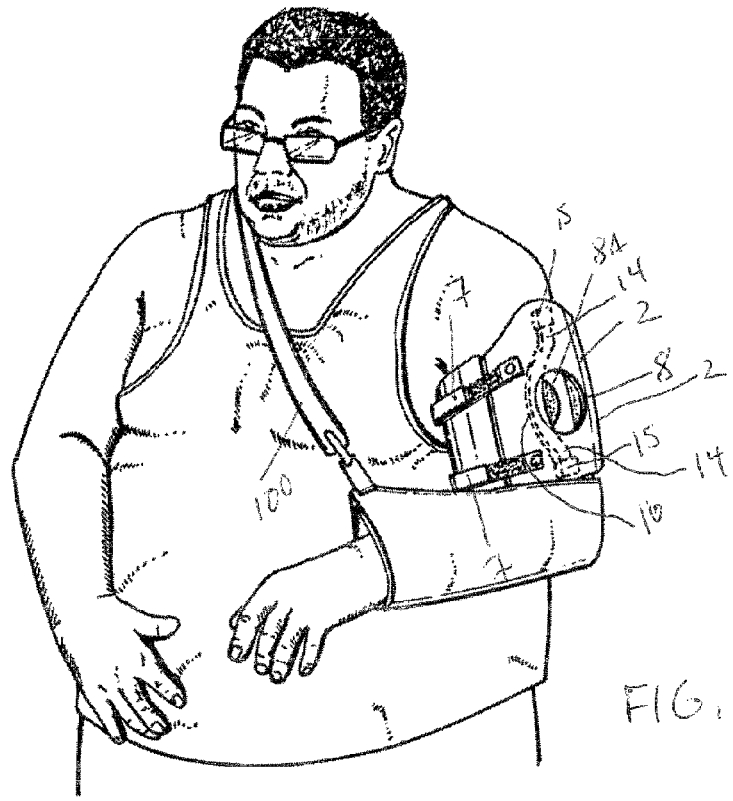
FIGS. 19 and 20 show an embodiment of the orthopaedic device for positioning and maintaining a localized pressure over a bone fracture in an obese patient.
Figure 20:
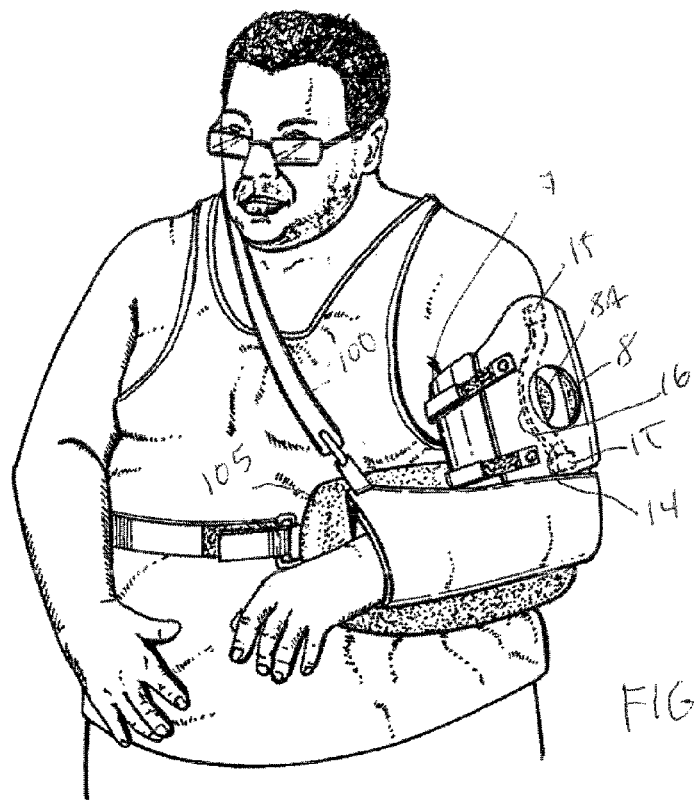

A sixth embodiment is described below with reference to FIGS. 19 and 20.

In the particular case of a morbidly obese patient, a special arrangement may be necessary to keep a localized pressure in place over a fracture since the weight of a limb or other body part may interfere with positioning of holder 2 (e.g., a brace or sling). A fracture of this type in an obese patient can be difficult to control with a single positioning device, such as a holder 2. A holder 2 alone typically cannot generate enough force to overcome the weight of the limb distal to the fracture. The use of an additional positioning device, such as a sling 100 or a pillow 105, is often helpful.

For example, in some morbidly obese patients, a humeral fracture can angulate over the torso, particularly when the fracture is in its mid-third and is unstable, i.e., transverse. In one configuration, as depicted in FIG. 19, this particular situation can be remedied by using a holder 2 (preferably, a BIO-CHEM BRACE) in the upper extremity in combination with an additional shoulder sling 100 for further support. In addition, an abdominal pillow 105 can be attached to the sling 100 to maintain the elbow away from the torso, as also shown in FIG. 20. Together, the holder 2 and the sling 100 together can supply the forces needed to maintain the localized pressure over the fracture.

Seventh Embodiment

An intermediate contact material such as 8A in FIG. 2 of the appropriate size, shape, thickness and density can be inserted above or below the electrical foil 23A in FIGS. 8-10 to achieve the desired pressure. This may require the holder 2 to be disengaged.

It is appreciated that the foil 23A may be used to apply the electric field without the need for charged foil elements 23b or 24. This embodiment allows different application schedules for the mechanical applied pressure, electrically applied pressure and the electric field.

Eighth Embodiment

An intermediate contact material such as 8A in FIG. 2 of the appropriate size, shape, thickness and density can be inserted above or below the flexible permanent magnetic strip element 29 in FIGS. 11-12 to achieve the desired pressure. This may require the holder 2 to be disengaged.

It is appreciated that the flexible permanent magnetic strip element 29 may be used to apply the magnetic field without the need for magnetic source elements 28 and 30. This embodiment allows different application schedules for the mechanical applied pressure, magnetically applied pressure and the magnetic field.

Ninth Embodiment

An intermediate contact material such as 8A in FIG. 2 of the appropriate size, shape, thickness and density can be inserted above or below the electrical foil 23A and the flexible permanent magnetic strip element 29, to achieve the desired pressure. This may require the holder 2 to be disengaged.

It is appreciated that the electrical foil 23A and the flexible permanent magnetic strip element 29 may be used to apply both an electric and magnetic field without the need for charged foil elements 23b or 24 or the magnetic source elements 28 and 30. This embodiment allows different application schedules for the mechanical applied pressure, electrically and magnetically applied pressure and electrical and magnetic field.

Numerous modifications and variations of the present invention are possible in light of the above teachings without departing from the spirit or scope of the invention. It is therefore to be understood that within the scope of the appended claims, the invention may be practiced otherwise than as specifically described herein.

What is claimed is:

1. An orthopaedic device for treating a bone fracture, the orthopaedic device comprising:
at least one pressure applying element configured to apply pressure to soft tissue adjacent to the bone fracture; and
a holder configured to engage, in an engaged configuration, soft tissue adjacent to the bone fracture and, while in the engaged configuration, to facilitate adjustable positioning and securing of the at least one pressure applying element to the holder,
wherein the at least one pressure applying element includes radiographic markers that function as markers in an x-ray image.

2. An orthopaedic device for treating a bone fracture, the orthopaedic device comprising:
at least one pressure applying element configured to apply pressure to soft tissue adjacent to the bone fracture; and
a holder configured to engage, in an engaged configuration, soft tissue adjacent to the bone fracture and, while in the engaged configuration, to facilitate adjustable positioning and securing of the at least one pressure applying element to the holder,
wherein:
the holder includes at least one access port extending through the holder to facilitate adjustable positioning and operation of the at least one pressure applying element within an engaged configuration of the holder, and
each of the at least one pressure applying element is comprised of a strip that is relatively flexible but inextensible, wherein the strip is releasably connected to the holder to define a length adjustable portion spanning across an access port and configured to be manipulated to apply radially directed pressure to a region of the soft tissue adjacent to the bone fracture.

3. An orthopaedic device according to claim 2, wherein each strip is further comprised of at least one ratcheting element, and each strip is releasably connected to the holder by an interlocking element configured to engage the at least one ratcheting element of each strip.

4. An orthopaedic device for treating a bone fracture, the orthopaedic device comprising:
at least one pressure applying element configured to apply pressure to soft tissue adjacent to the bone fracture; and
a holder configured to engage, in an engaged configuration, soft tissue adjacent to the bone fracture and, while in the engaged configuration, to facilitate adjustable positioning and securing of the at least one pressure applying element to the holder,
wherein:
the holder includes at least one access port extending through the holder to facilitate adjustable positioning and operation of the at least one pressure applying element within an engaged configuration of the holder, and
each of the at least one pressure applying element is comprised of a load-adjustable spring element configured to be adjustably positioned on the holder through an access port, and a connecting mechanism attached to the load-adjustable spring element and configured to operatively connect the load-adjustable spring element to the holder and to adjust the bias on the load-adjustable spring element to adjust the radially directed pressure applied to the soft tissue adjacent to the bone fracture.

5. An orthopaedic device for treating a bone fracture, the orthopaedic device comprising:
at least one pressure applying element configured to apply pressure to soft tissue adjacent to the bone fracture; and
a holder configured to engage, in an engaged configuration, soft tissue adjacent to the bone fracture and, while in the engaged configuration, to facilitate adjustable positioning and securing of the at least one pressure applying element to the holder,
wherein:
the holder includes at least one access port extending through the holder to facilitate adjustable positioning and operation of the at least one pressure applying element within an engaged configuration of the holder, and
each of the at least one pressure applying element is comprised of a bladder containing a liquid, gas or a solidifiable liquid, wherein the bladder is configured to be adjustably positioned to the holder through at least one access port and to be molded in form to protrude toward and to apply a radially directed pressure to the soft tissue adjacent to the bone fracture.

6. An orthopaedic device according to claim 5, wherein the bladder is configured to contain a solidifiable liquid that is a magnetorheological fluid.

7. An orthopaedic device according to claim 5, wherein the bladder is configured to contain a solidifiable liquid that is an electrorheological fluid.

8. An orthopaedic device for treating a bone fracture, the orthopaedic device comprising:
at least one pressure applying element configured to apply pressure to soft tissue adjacent to the bone fracture; and
a holder configured to engage, in an engaged configuration, soft tissue adjacent to the bone fracture and, while in the engaged configuration, to facilitate adjustable positioning and securing of the at least one pressure applying element to the holder,
wherein:
the holder includes at least one access port extending through the holder to facilitate adjustable positioning and operation of the at least one pressure applying element within an engaged configuration of the holder, and
each of the at least one pressure applying element is comprised of
at least one foil element, configured to hold a first electric charge and having a first and second interconnected portions further configured to repel from one another to thereby apply pressure to soft tissue adjacent to the bone fracture; and
a foil element configured to hold a second electric charge of an opposing polarity to the first electric charge,
wherein the foil elements are configured to direct calcium ions toward the bone fracture,
wherein the foil elements are positioned through at least one access port and secured to the holder.

9. An orthopaedic device according to claim 8, further comprising a controller to modulate the electric charge held on the foil elements based on a predetermined profile pattern.

10. An orthopaedic device for treating a bone fracture, the orthopaedic device comprising:
at least one pressure applying element configured to apply pressure to soft tissue adjacent to the bone fracture; and
a holder configured to engage, in an engaged configuration, soft tissue adjacent to the bone fracture and, while in the engaged configuration, to facilitate adjustable positioning and securing of the at least one pressure applying element to the holder,
wherein:
the holder includes at least one access port extending through the holder to facilitate adjustable positioning and operation of the at least one pressure applying element within an engaged configuration of the holder, and
each of the at least one pressure applying element is comprised of:
a magnetic source configured to produce an adjustable magnetic field; and
a flexible permanent magnetic strip element configured to be adjustably positioned to the holder through one access port,
wherein the flexible permanent magnetic strip element is operatively associated with the magnetic source to apply pressure to the soft tissue adjacent to the fracture.

11. An orthopaedic device according to claim 10, further comprising a controller to modulate the magnetic field produced by the magnetic source based on a predetermined profile pattern.

12. A method of treating a bone fracture with an orthopaedic device having a holder and at least one pressure applying element configured to apply pressure to soft tissue adjacent to a bone fracture, the method comprising:
configuring the holder into an engaged configuration to engage soft tissue adjacent to the bone fracture; and
while the holder is in the engaged configuration, adjustably positioning and securing the at least one pressure applying element to the holder,
wherein the step of adjustably positioning and securing the at least one pressure applying element to the holder while the holder is in an engaged configuration further comprises adjustably positioning each of the at least one pressure applying element to the holder through at least one access port disposed on and extending through the holder.

13. A method of treating a bone fracture according to claim 12, wherein the at least one pressure applying element is comprised of a strip that is relatively flexible but inextensible, the method further comprising adjustably positioning and securing the strip to the holder such that a length adjustable portion of the strip spans across one of the at least one access port and adjusting the length adjustable portion of the strip into a convex shape to thereby adjust the radially directed pressure applied to a region of the soft tissue adjacent to the bone fracture.

14. A method of treating a bone fracture according to claim 12, wherein the at least one pressure applying element is comprised of a load-adjustable spring element attached to a connecting mechanism, the method further comprising adjustably positioning the load-adjustable spring element to the holder through one of the at least one access port, connecting the connecting mechanism to the holder, and configuring the connecting mechanism to adjust the bias on the load-adjustable spring element to thereby adjust the radially directed pressure applied to the soft tissue adjacent to the bone fracture.

15. A method of treating a bone fracture according to claim 12, wherein the at least one pressure applying element is comprised of at least one foil element having a first and second interconnected portion, each portion configured to have a positive charge, and a foil element configured to have a negative charge, the method further comprising
adjustably positioning the at least one foil element configured to have a positive charge to the holder through one of the at least one access port,
applying a positive charge to the at least one foil element configured to have a positive charge whereby the first and second interconnected portions of each of the at least one foil element repels from one another to apply pressure to the soft tissue adjacent to the bone fracture;
applying a negative charge to the foil element configured to have a negative charge whereby calcium ions within the soft tissue are directed toward the bone fracture.

16. A method of treating a bone fracture according to claim 12, wherein the at least one pressure applying element is comprised of a magnetic source configured to produce an adjustable magnetic field, and a flexible permanent magnetic strip element, the method further comprising
adjustably positioning the flexible permanent magnetic strip element to the holder through one of the at least one access port;
securing the flexible permanent magnetic strip element to the holder such that at least a portion of the permanent magnetic strip element can protrude toward and apply pressure to a region of the soft tissue adjacent to the bone fracture; and activating the magnetic source to attract or repulse the flexible permanent magnetic strip to thereby apply pressure to a region of the soft tissue adjacent to the bone fracture, and to direct calcium ions within the soft tissue toward the bone fracture.

17. A method of treating a bone fracture with an orthopaedic device having a holder and at least one pressure applying element configured to apply pressure to soft tissue adjacent to a bone fracture, the method comprising:
configuring the holder into an engaged configuration to engage soft tissue adjacent to the bone fracture;
while the holder is in the engaged configuration, adjustably positioning and securing the at least one pressure applying element to the holder; and
detachably attaching an intermediary contact material to the at least one pressure applying element such that the intermediary contact material transmits and distributes the radially directed pressure applied by the at least one pressure applying element to the soft tissue adjacent to a bone fracture.

18. An orthopaedic device for treating a bone fracture, the orthopaedic device comprising:
at least one pressure applying element configured to apply pressure to soft tissue adjacent to the bone fracture;
a holder configured to engage, in an engaged configuration, soft tissue adjacent to the bone fracture and, while in the engaged configuration, to facilitate adjustably positioning and securing the at least one pressure applying element to the holder;
at least one foil element configured to hold a first electric charge and adjustably positioned to the at least one pressure applying element; and
a foil element configured to hold a second electric charge of an opposing polarity to the first electric charge and adjustably positioned to the holder,
wherein the at least one foil element having a first electric charge and the foil element having a second electric charge are configured such that an adjustable voltage potential difference exists between the at least one foil element having a first electric charge and the foil element having a second electric charge.

* * * * *